United States Patent
Song

(10) Patent No.: US 10,927,090 B2
(45) Date of Patent: Feb. 23, 2021

(54) BUAGAFURAN ACTIVE PHARMACEUTICAL INGREDIENT, PREPARATION METHOD AND APPLICATION THEREOF

(71) Applicant: Beijing Union Pharmaceutical Factory, Beijing (CN)

(72) Inventor: Bo Song, Beijing (CN)

(73) Assignee: BEIJING UNION PHARMACEUTICAL FACTORY, Beijing (CN)

( * ) Notice: Subject to any disclaimer, the term of this patent is extended or adjusted under 35 U.S.C. 154(b) by 0 days.

(21) Appl. No.: 16/344,026

(22) PCT Filed: Apr. 18, 2018

(86) PCT No.: PCT/CN2018/083526
§ 371 (c)(1),
(2) Date: Apr. 23, 2019

(87) PCT Pub. No.: WO2018/214676
PCT Pub. Date: Nov. 29, 2018

(65) Prior Publication Data
US 2019/0337913 A1 Nov. 7, 2019

(30) Foreign Application Priority Data

May 23, 2017 (CN) .......................... 201710369327.X

(51) Int. Cl.
*A61P 25/00* (2006.01)
*C07D 307/00* (2006.01)
*A61K 47/32* (2006.01)

(52) U.S. Cl.
CPC ............ *C07D 307/00* (2013.01); *A61K 47/32* (2013.01)

(58) Field of Classification Search
CPC ...................................................... A61P 25/00
See application file for complete search history.

(56) References Cited

U.S. PATENT DOCUMENTS 6,486,201 B1    11/2002  Guo et al.
2020/0095219 A1*  3/2020  Zhong .................. C07D 307/77

FOREIGN PATENT DOCUMENTS

| CN | 1254713 A | 5/2000 |
| CN | 1322525 A | 11/2001 |
| CN | 1199960 C | 5/2005 |
| EP | 1132383 B1 | 5/2010 |
| JP | 4321967 B2 | 8/2009 |

OTHER PUBLICATIONS

Demidova, Yu.S. et al. "Selective carvone hydrogenation to dihydrocarvone over titania supported gold catalyst." Catalysis Today. (2015), vol. 241, pp. 189-194. (Year: 2015).*
Liu, Qian et al., Synthesis and CNS Activities of a-agarofuran Derivatives. Chinese Journal of Medicinal Chemistry, Jun. 30, 2003, 13(3), pp. 125-130.
Yin, Da-Li et aL., Stereoselective Synthesis of an Anxiolytic Candidate— AF-5 from(+)-dihydrocarvone. Chinese Journal of Medicinal Chemistry,Aug. 2003 vol. 13, No. 4, pp. 187-193, China Academic Journal Electronic Publishing House.
Li, Chun, et al. New Stereoselective Synthesis of 4-Butyl-a-agarofuran, Chinese Chemical Letters vol. 14, No. 9 , pp. 881-882 , 2003.
Wu, Xiang-Hong, et al. Efficient and Large-Scale Synthesis of an Intermediate of AF-5:(4aR,7R)-1-Butyl-4a-methyl-7-(1-methy-1-hydroxyethyl)-2(1H)-octalone, Chemical Research, Dec. 2005. vol. 16, No. 4, p. 10-12.
Xia,Xue-Jun et al., Analysis and Identification of Degradation Products of Buagafuran by High Performance Liquid Chromatography-diode Array Detection-tandem Mass Spectrometry, Acta Pharmaceutica Sinica. Aug. 31, 2013, 48 (8), pp. 1292-1296.
Xia,Xue-Jun et al. Preparation and in vitro Study of Buagafuran Solid Dispersions. Acta Pharmaceutica Sinica.May 31, 2008,43(5), pp. 548-552.

* cited by examiner

*Primary Examiner* — John S Kenyon
(74) *Attorney, Agent, or Firm* — Bayramoglu Law Offices LLC

(57) ABSTRACT

A method suitable for large-scale production of buagafuran active pharmaceutical ingredient. A buagafuran active pharmaceutical ingredient (API) with a high purity prepared by the method includes an active ingredient of buagafuran, an impurity A, and an impurity B. In the buagafuran API, a content of the active ingredient of buagafuran is higher than 97.5%, and a total content of the impurity A and the impurity B is less than 0.04%. The buagafuran API can be applied to new drug development processes such as clinical research, pharmaceutical research and quality control research.

2 Claims, 2 Drawing Sheets

| Zhejiang Warrant Pharmaceutical Co., Ltd. | Record number: TS-QS-4010a |
| --- | --- |
| | Version number: 01 |
| Address: Xingbin Road, Binhai Industrial Zone, Keqiao District, Shaoxing City, Zhejiang Province | Phone Number: +86-575-85593529 ; Fax Number: +86-575-85593531 |

Product Inspection Report

No.:41608010

Page 1 of 2

| Product Name | Buagafuran | Specifications/dosage form | Active Pharmaceutical Ingredient |
| --- | --- | --- | --- |
| Batch Number | 160601 | Package | / |
| Quantity | 1.62kg | Source | First Workshop |
| Production Date | 24, July, 2016 | Valid Until | 23, July, 2018 |
| Sampling Date | 27, July, 2016 | Report Date | 03, August, 2016 |
| Inspection Basis | TS-QS-4010-00/ SOP-T-4010-00 | | |

Inspection Items and Results

| Inspection Items | Standard Regulation | Inspection Results |
| --- | --- | --- |
| [Character] | | |
| Appearance | White to light yellow solid (2 °C - 8 °C) | White solid |
| | Colorless to pale yellow oily liquid (25 ± 2 °C) | Colorless oily liquid |
| Solubility | Easily soluble in acetone, ether, chloroform, methanol, ethanol, soluble in acetonitrile, almost insoluble in water | Compliance |
| Specific Rotation | Not less than +22.0° | +22.5° |
| Refractive Index | 1.490~1.510 | 1.494 |
| [Identification] | | |
| HPLC | The retention time of the main peak of the test product solution should be consistent with the retention time of the main peak of the comparison product solution | Consistent with the retention time of the main peak of the comparison product solution |
| IR | The infrared absorption spectrum of the test product should be consistent with the infrared absorption spectrum of the comparison product | Consistent with the infrared absorption spectrum of the comparison product |
| Color Reaction | Should present positive reaction | Positive reaction |
| [Inspection] | | |
| Moisture | Not more than 0.50% | 0.16% |
| Clarity and color of the solution | It should be clarified as colorless; if it is turbid, it should not be more concentrated than the turbidity standard solution No. 1; if it is colored, it should not be deeper than the yellow or yellow-green color standard solution No. 3. | The solution is clear and colorless |
| Chloride | Not more than 0.02% | Compliance |
| Sulfate | Not more than 0.02% | Compliance |
| Relative Substance | The maximum single impurity must not exceed 1.0% | 0.031% |
| | Total impurities must not exceed 2.5% | 0.060% |

FIG. 1

| Zhejiang Warrant Pharmaceutical Co., Ltd. | Record number: TS-QS-4010a |
| | Version number: 01 |
| Address: Xingbin Road, Binhai Industrial Zone, Keqiao District, Shaoxing City, Zhejiang Province | Phone Number: +86-575-85593529 ; Fax Number: +86-575-85593531 |

Product Inspection Report    No.:41608010

Page 2 of 2

| Product Name | Buagafuran | Specifications/dosage form | Active Pharmaceutical Ingredient |
|---|---|---|---|
| Batch Number | 160601 | Package | / |
| Quantity | 1.62kg | Source | First Workshop |
| Production Date | 24, July, 2016 | Valid Until | 23, July, 2018 |
| Sampling Date | 27, July, 2016 | Report Date | 03, August, 2016 |
| Inspection Basis | TS-QS-4010-00/ SOP-T-4010-00 | | |

Inspection Items and Results

| Inspection Items | Standard Regulation | Inspection Results |
|---|---|---|
| Enantiomer | Must not exceed 1.0% | 0.018% |
| Residual Solvent | Methanol must not exceed 3000 ppm | Not detected |
| | Ethanol must not exceed 60000 ppm | 26269ppm |
| | Tert-butanol must not exceed 1000 ppm | Not detected |
| | Normal hexane must not exceed 230 ppm | Not detected |
| | Isopropyl ether must not exceed 1000 ppm | Not detected |
| | Ethyl acetate must not exceed 5000 ppm | Not detected |
| Residue on Ignition | Must not exceed 0.20% | 0.030% |
| Heavy Metal | Not more than twenty parts per million | Compliance |
| Microbial Limit | The total number of aerobic bacteria must not exceed 1000 CFU/g | <10CFU/g |
| | The total number of molds and yeasts must not exceed 100 CFU/g | <10CFU/g |
| | *Escherichia coli* should not be detected /g | Not detected |
| [Content] (calculated as anhydrous, solvent-free) | 97.0~102.0% | 97.7% |

| Conclusion | This product is inspected according to SOP-T-4010-00, and the results meet the requirements of TS-QS-4010-00 quality standard |
|---|---|

Inspector:    Checker:    QC Minister:
Date: 2016-08-03    Date: 2016-08-03    Date: 2016-08-03

FIG. 2

BUAGAFURAN ACTIVE PHARMACEUTICAL INGREDIENT, PREPARATION METHOD AND APPLICATION THEREOF

CROSS REFERENCE TO THE RELATED APPLICATIONS

This application is the national phase entry of International Application No. PCT/CN2018/083526, filed on Apr. 18, 2018, which is based upon and claims priority to Chinese Patent Application No. 201710369327.X, filed on May 23, 2017, the entire contents of which are incorporated herein by reference.

TECHNICAL FIELD

The present invention belongs to the technical field of medicine, and particularly relates to a buagafuran active pharmaceutical ingredient (API), a preparation method and an application thereof.

BACKGROUND

Buagafuran is a derivative of the active ingredient α-agarofuran derived from agarwood (*Aquillaria agallocha* Roxb). by researchers of the Institute of Materia Medica, Chinese Academy of Medical Sciences. Buagafuran has been proven to have the effects of anti-anxiety, anti-depression and relieving sleep disorders, meanwhile, buagafuran has low toxicity, and is a new candidate drug of category 1.1 with independent intellectual property rights in China (Chinese Patent No. ZL98122447.4, U.S. Pat. No. 6,486,201B1, European Patent No. EP1132383B1, Japanese Patent No. 4321967). The Applicant of the present invention has obtained the patent assignment and the clinical research permission transfer of the buagafuran from the Institute of Materia Medica, and is carrying out the second phase of clinical research work (The drug clinical trial permission number is: 2014L00180, 2014L0018).

The existing reported preparation methods of buagafuran mainly include the following strategies:

Route 1:

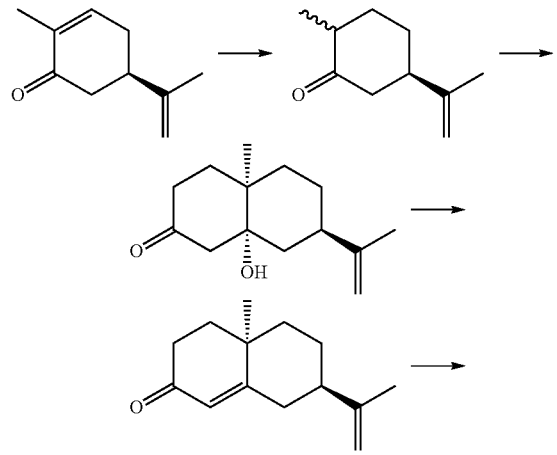

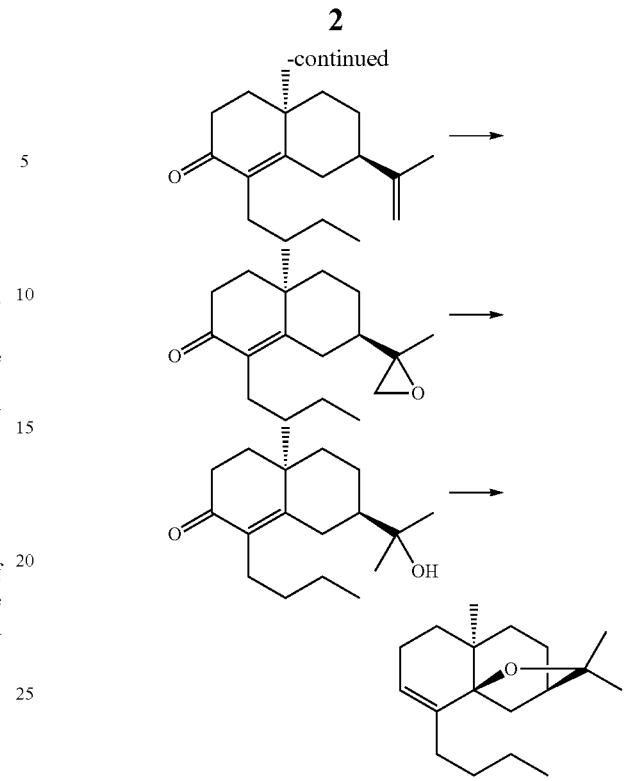

Using L-carvone as a raw material, buagafuran was obtained through 7 steps of reduction, Robinson cyclization, dehydration, alkylation, epoxidation, reduction and cyclization successively (Qian Liu et al., Chinese Journal of Medicinal Chemistry, 13(3): 125-130). However, when the Applicant reproduced the preparation process, it was found that the terminal methyl group was easily removed during the epoxidation process of the double bond in the fifth step. It is difficult to avoid by-products of terminal methyl group removal during the pilot production, resulting in the final product contains a by-product missing one methyl group on the bridged ring. The properties of this by-product are very similar to the properties of buagafuran, thus it is difficult to remove the by-product, and reduces the quality of the buagafuran API. In addition, the expensive $LiAlH_4$ is used in the reduction of the epoxy group, resulting in an undesired cost increase.

Route 2:

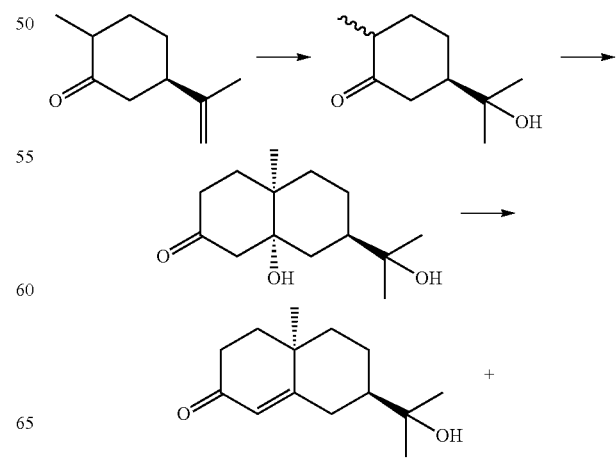

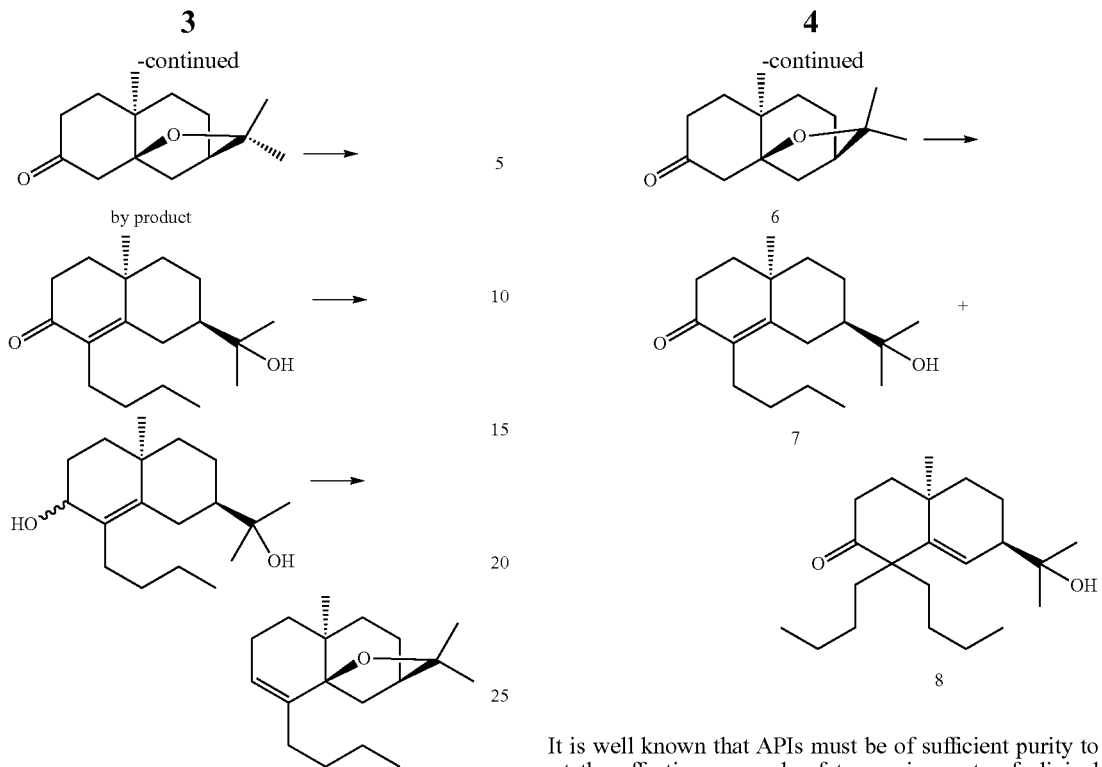

Using L-dihydrocarvone as a raw material, buagafuran is obtained through 6 steps of oxidation, cyclization, dehydration, alkylation, reduction and cyclization successively. However, a cyclized by-product is produced in the third step of dehydration reaction in this route. In view of this, it is reported in the above reference that the reaction needs to be carried out in a two-phase system containing water and n-hexane or a two-phase system containing water and petroleum ether. Due to the polarity difference between the target intermediate compound 5 and the cyclized by-product 6, the target intermediate compound 5 and the cyclized by-product 6 respectively exist in one of the two phases in the reaction system. However, a structure conversion between the target intermediate compound 5 and the cyclized by-product 6 can occur, and when the mixed solution of the target intermediate compound 5 and the cyclized by-product 6 is directly subjected to a butylation reaction to prepare the compound 7, the dibutylated impurity 8 is obtained (Dali Yin et al., Chinese Journal of Medicinal Chemistry, 13(4): 187-193; Chun Li et al., Chinese Chemical Letters, 14(9): 881-882). Subsequently, by optimizing the alkaline condition and the amount of the butylating agent in the butylation process, the yield of the target compound 7 in the optimal scheme is only 69.8%, and 15% of the dibutylated impurity 8 is still contained (Xianghong Wu et al., Chemical Research, 16(4): 10-12).

It is well known that APIs must be of sufficient purity to meet the effectiveness and safety requirements of clinical applications. Moreover, in the process from the clinical research to the future production and marketing, it is necessary to prepare enough samples and complete the related pharmaceutical research work. However, the existing preparation methods are all laboratory-level small-scale tests, and the column chromatography method is required to be performed for intermediate purification several times in the steps. It is difficult to meet the needs of mass production, and there is a high content of impurities. Moreover, buagafuran has special physical and chemical properties, and is in the form of oil at room temperature, so it is difficult to remove the impurities. Therefore, it is necessary to study the method of large-scale preparation of buagafuran API to obtain high-purity buagafuran API samples, clarify the structures of the impurities, and control the content of the impurities, so that the API samples can be applied in new drug development processes such as clinical research, pharmaceutical research and quality control research.

SUMMARY

The objective of the present invention is to obtain a method suitable for large-scale production of buagafuran active pharmaceutical ingredient (API). By the method, a high-purity buagafuran API can be obtained and applied in a subsequent research process.

Specifically, the present invention provides a buagafuran API, wherein the active ingredient, i.e., buagafuran, has the following structure:

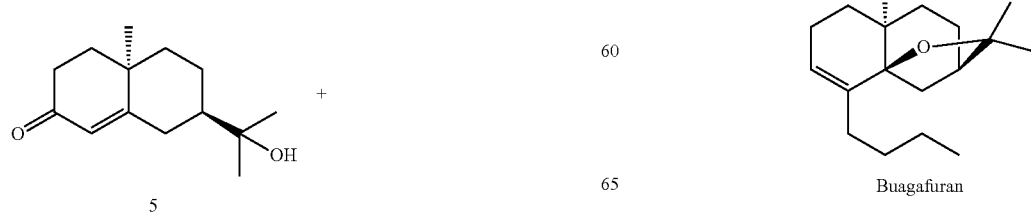

Buagafuran

In another aspect, the present invention provides a buagafuran API, wherein in addition to the active ingredient, i.e., buagafuran, the buagafuran API further contains impurities having the following structure:

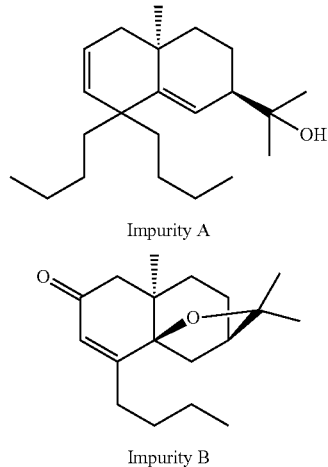

Impurity A

Impurity B

Moreover, in the buagafuran API, the content of the active ingredient, i.e., buagafuran, is higher than 97.5%, and the total content of the impurity A and the impurity B is less than 0.04%. In particular, a certain amount of solvent remains in the buagafuran API, and the residual solvent is preferably ethanol. In particular, a certain enantiomer of buagafuran remains in the buagafuran API, and the enantiomer is derived from a small amount of enantiomer impurities present in the starting material of the synthesis. Preferably, the content of the buagafuran enantiomer impurities remaining in the API is not more than 0.02%.

In another aspect, the present invention provides a pharmaceutical composition including the buagafuran API of the present invention and a pharmaceutically acceptable carrier. Preferably, the pharmaceutically acceptable carrier includes polyvinylpyrrolidone, and more preferably, the polyvinylpyrrolidone is PVP-K30. Preferably, the pharmaceutical composition is in the form of oral preparation, and more preferably, the oral preparation is a capsule.

In another aspect, the present invention provides a method of preparing a buagafuran API of the present invention, which includes the following steps:

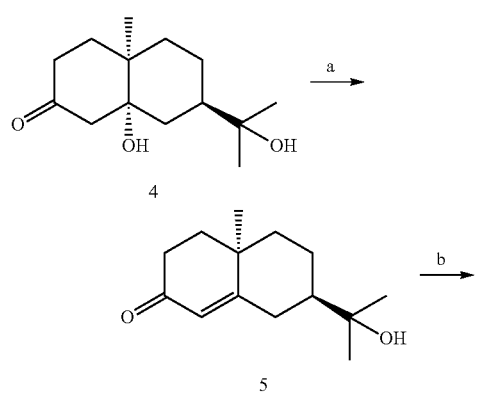

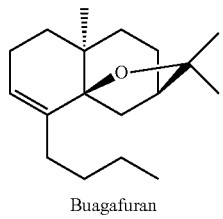

Buagafuran

Specifically, the step a includes adding the compound 4 to a potassium hydroxide aqueous solution, heating and stirring, cooling after the completion of the reaction, adding concentrated hydrochloric acid to adjust a pH of the mixture to near-neutral, and then performing extraction, drying, filtration and filtrate concentration. The step b includes dissolving the compound 5 in tert-butanol, and then adding to a potassium hydroxide aqueous solution, heating and stirring, adding bromobutane, adjusting a pH to near-neutral, filtering, concentrating the filtrate, dissolving the concentrate in methanol, adding sodium borohydride, stirring, adding n-hexane and water to adjust a pH of the system to acidity, separating out the n-hexane layer, and concentrating to obtain a crude buagafuran.

In particular, after the pH of the system is adjusted to acidity, the separated n-hexane layer contains the impurity A and the impurity B in addition to the crude buagafuran:

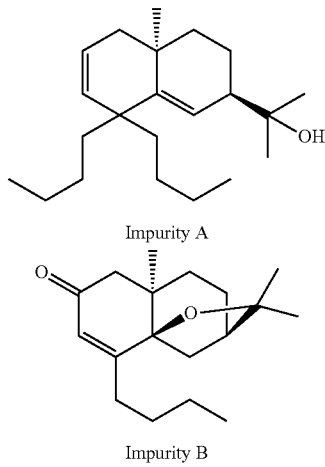

Impurity A

Impurity B

Preferably, the total content of the impurities A and B in the crude buagafuran is not more than 3.5%.

Preferably, the compound 4 is prepared by the following method:

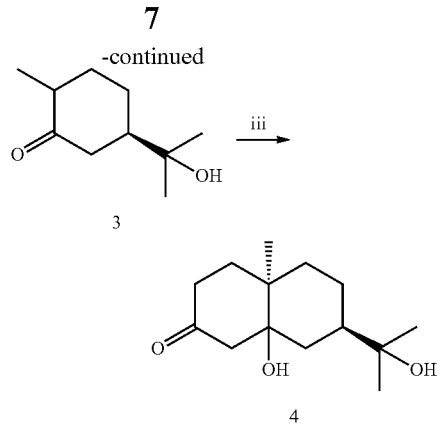

Specifically, the step i is a reduction reaction; the step ii is an oxidation reaction; and the step iii is a cyclization reaction of compound 3 with methyl vinyl ketone. Preferably, in the reduction reaction of step i, zinc powder is used as a catalyst; in the oxidation reaction of step ii, concentrated sulfuric acid is used as an oxidizing agent; and the cyclization reaction of step iii contains an alkaline reagent, i.e., potassium hydroxide.

In another aspect, the present invention provides a method for refining the buagafuran API of the present invention, including the following steps: dissolving the crude buagafuran in ethanol, filtering, and cooling the filtrate to −10° C. to −20° C., then performing suction filtration to obtain a wet product of refined buagafuran, drying the wet product to obtain the buagafuran API.

In another aspect, the present invention provides an application of the buagafuran API of the present invention as a standard substance in pharmaceutical research of buagafuran.

In another aspect, the present invention provides an application of the impurity A in the quality control of buagafuran medicine, wherein the impurity A is used as a comparison substance for the impurity detection of buagafuran.

In another aspect, the present invention provides an application of the impurity B in the quality control of buagafuran medicine, wherein the impurity B is used as a comparison substance for the impurity detection of buagafuran.

In another aspect, the present invention provides applications of the impurities A and B in the quality control of buagafuran medicine, wherein the impurities A and B are used as comparison substances for the impurity detection of buagafuran.

In another aspect, the present invention provides an application of the buagafuran API in the preparation of a medicament for treating mental disorders, wherein the mental disorders include anxiety, depression or sleep disorder.

BRIEF DESCRIPTION OF THE DRAWINGS

FIG. 1 is a diagram showing Part I of a quality inspection report of a buagafuran API provided by an entrusted manufacturer; and FIG. 2 is a diagram showing Part II of the quality inspection report of the buagafuran API provided by the entrusted manufacturer.

DETAILED DESCRIPTION OF THE EMBODIMENTS

The present invention will be further described in detail below along with specific embodiments. The following embodiments are used for the understanding of the method and the core idea of the present invention, and any possible variation or substitution made by those skilled in the art without departing from the inventive concept of the present invention shall fall within the protective scope of the present invention.

All the operations of the preparation process in the present invention are entrusted to Zhejiang Warrant Pharmaceutical Co., Ltd. to complete in a GMP workshop, and the product quality inspection is carried out in accordance with the GMP management regulations. Unless otherwise specified, the raw materials and reagents used in the present invention are all chemically pure or have higher purity.

Embodiment 1 Preparation of Buagafuran API (1) Synthesis of Compound 2

Under stirring, 40.8 kg of drinking water and 16.3 kg of potassium hydroxide were successively added until dissolved completely, and then 98.0 kg of methanol and 32.6 kg of zinc powder were sequentially added. The mixture was heated, refluxed and stirred, and L-carvone methanol solution was added slowly, then refluxed and stirred until the reaction is completed. Subsequently, the mixture was cooled, and filtered, and filter cake was rinsed with water. The temperature is controlled not to exceed 65° C., and the filtrate was decompressed and concentrated to remove methanol. The residue was stand and cooled, and then the oil layer was separated. The aqueous layer was extracted with n-hexane. The oil layer was combined with n-hexane, and washed with drinking water to near neutrality. Drying and filtering were performed, and the n-hexane was subjected to reduced pressure distillation. The remaining material was continuously subjected to reduced pressure rectification with a high vacuum pump to distill a fraction having a boiling point of 60° C.–70° C. (2-3 mmHg of fraction) to obtain the compound 2 (bp 74° C./2 mmHg, nd 1.470, yield: 86.2%).

(2) Synthesis of Compound 3

31.6 kg of concentrated sulfuric acid was slowly added to 37.0 kg of drinking water under stirring, compound 2 was added, and stirring was continued until the reaction was completed. The mixture was extracted with n-hexane, washed, dried, filtered, and subjected to reduced pressure distillation. After the reduced pressure distillation was completed, 44.1 kg of isopropyl ether was continuously pumped into the mixture, stirred until dissolved completely to obtain the compound 3 isopropyl ether mixture. Compound 3: EI MS (m/z) 170 (M$^+$).

(3) Synthesis of Compound 4

The compound 3 isopropyl ether mixture obtained in the previous step was added under stirring. After the addition, the mixture was further stirred and cooled to 0° C.–10° C., and a pre-prepared potassium hydroxide/ethanol solution (a solution prepared with 1.9 kg of potassium hydroxide and 5.7 kg of ethanol) was slowly added to the system. After the addition of the pre-prepared potassium hydroxide/ethanol solution, the stirring was continued. The mixture was cooled to about −10° C., and a mixed solution of methyl vinyl ketone and isopropyl ether (including 6.7 kg of methyl vinyl ketone and 16.5 kg of isopropyl ether) was added dropwise. After the dropwise addition was completed, the reaction mixture was continuously stirred, and 3.3 kg of concentrated hydrochloric acid was added slowly to adjust the pH of the system to near neutrality. The suction filtration was carried out, and the filter cake was rinsed with isopropyl ether and dried under vacuum at room temperature to obtain compound 4 (yield: 83.3%).

Compound 4: $[\alpha]_D^{15}=+56.9°$; $^1$HNMR (400 MHz, CD$_3$OD, δ): 2.83 (d, 1H), 2.60 (dt, 1H), 2.16-1.97 (m, 3H), 1.83-1.68 (m, 2H), 1.56-1.51 (m, 1H), 1.47-1.42 (m, 1H), 1.36-1.20 (m, 4H), 1.13 (s, 3H), 1.06 (s, 6H); $^{13}$CNMR (100 MHz, CD$_3$OD, δ): 212.6 (C=O), 76.3 (C—OH), 72.8 (C—OH), 54.3, 44.3, 38.4, 37.7, 36.8, 35.8, 32.8, 27.3, 27.2, 22.6, 22.1; EI MS (m/z): 240 (M$^+$), 222 ([M-H$_2$O]$^+$), 207, 164, 149, 126.

(4) Synthesis of Compound 5

Under stirring, 41.8 kg of drinking water and 2.2 kg of potassium hydroxide were added in sequence. The compound 4 obtained in the previous step was slowly added. The mixture was continuously stirred, heated and refluxed until the reaction was completed. Then the mixture after the reaction was cooled, and the concentrated hydrochloric acid was added to adjust the system to near neutrality. The mixture was extracted with dichloromethane, dried, and filtered, and the reduced pressure distillation was performed to recover dichloromethane. Subsequently, 8.0 kg of tert-butanol was added to obtain the compound 5/tert-butanol mixture for the next reaction.

Compound 5: $^1$H NMR (CDCl$_3$, δ) 5.80 (s, 1H), 1.09-2.65 (m, 11H), 1.30 (s, 3H), 1.18 (s, 3H), 1.15 (s, 3H); EI MS (m/z) 222 (M$^+$).

(5) Synthesis of Buagafuran 2.8 kg of potassium hydroxide was dissolved in 59.5 kg of tert-butanol under stirring until dissolved completely, and the compound 5/tert-butanol solution obtained in the previous step was added. After the addition, the mixture was heated to reflux, a mixture of bromobutane and tert-butanol (including 6.2 kg of bromobutane and 4.5 kg of tert-butanol) was added dropwise, and the stirring was continued until the reaction was completed. The mixture was cooled, and the concentrated hydrochloric acid was added to adjust the system to near neutral. The filtering was performed, and the filtrate was decompressed and concentrated. 31.0 kg of methanol was added into the residual viscous material until residual viscous material was dissolved completely, and 2.7 kg of sodium borohydride was added until the reaction was completed. 10.0 kg of drinking water was added and the stirring was continued. Further, 39.0 kg of n-hexane was added, and the stirring was continued. The pH of the system was adjusted to 3.0 to 4.0 with hydrochloric acid, and then the stirring was continued until the reaction was completed. The mixture was stand for delamination, and n-hexane layer was taken, washed with water, dried, and filtered. The filtrate was decompressed and concentrated, and purified by silica-gel column chromatography with the eluent of a mixture containing petroleum ether and ethyl acetate having a ratio of 40-80:1, so that the crude buagafuran was obtained in a yield of 85.2%. Impurity A and impurity B were also collected during the column chromatography. The yield of the impurity A was 1.9%; and the yield of the impurity B was 1.3%.

Buagafuran: $[\alpha]_D^{20}=+22.5°$ (absolute ethanol), $^1$H NMR (500 MHz, CDCl$_3$, δ) 0.92 (s, 3H), 0.92 (t, 3H), 1.05 (dd, 1H), 1.19 (dd, 1H), 1.24 (s, 3H), 1.28-1.45 (m, 4H), 1.36 (s, 3H), 1.60-1.71 (m, 4H), 1.75 (dd, 1H), 1.80-2.05 (m, 5H), 2.22 (dd, 1H), 5.58 (dd, 1H); $^{13}$C NMR (100 MHz, CDCl$_3$, δ) 85.27, 136.37, 125.91, 22.48, 32.91, 36.92, 34.47, 24.41, 44.10, 80.74, 32.60, 30.77, 22.83, 31.27, 14.06, 21.89, 22.83, 30.34; EI MS (m/z) 262 (M$^+$).

Impurity A: $^1$H NMR (500 MHz, CDCl$_3$, δ): 0.88 (t, 6H); 1.06 (s, 3H); 1.20-1.41 (m, 20H); 1.76-2.02 (m, 5H); 4.49 (s, 1H); 5.29 (s, 1H); 5.37 (d, J=5.3 Hz, 1H); 5.51 (d, J=5.3 Hz, 1H); EI MS (m/z) 318 (M$^+$).

Impurity B: $^1$H-NMR (500 MHz, CDCl$_3$, δ): 0.93 (t, 3H), 1.04 (s, 3H), 1.30 (s, 3H), 1.43 (s, 3H), 1.98 (d, 1H), 2.76 (d, 1H), 5.91 (br.s, 1H); EI MS (m/z) 276 (M$^+$).

(6) Refining of Buagafuran The ethanol was added to the crude buagafuran, the mixture was stirred at room temperature for dissolution, and filtering was performed. The solution was cooled to −20° C. to −10° C., stirred for 30 minutes while keeping the temperature, and suction filtration was performed. A wet product of the buagafuran finished product was obtained. The wet product was dried at a vacuum degree greater than or equal to −0.090 Mpa, the drying temperature was 20° C. to 30° C., and the yield is 87.2%. After detecting, the purity of buagafuran in the refined product was greater than or equal to 97.5%, and the total content of impurity A and impurity B was less than or equal to 0.04%. The buagafuran API refined product has a certain amount of ethanol residue and the buagafuran enantiomer impurity not higher than 0.02%.

Conclusion: The total yield of the buagafuran API obtained through the steps described in Embodiment 1 was 24.3±5.8%.

Embodiment 2 Preparation of Buagafuran Capsules (1) Prescription (Calculated According to the Preparation of 1000 Capsules):

| Raw materials | additive amount |
| --- | --- |
| Buagafuran | 10 g |
| Povidone (PVP k-30) | 150 g |
| Anhydrous ethanol | 500 mL |
| Total | 1000 capsules |

(2) Preparation Process of Capsules

The buagafuran and PVP K-30 were weighed according to the prescribed amount and placed in a round-bottom flask, and anhydrous ethanol was added thereto. The mixture was stirred until completely dissolved, and then rotary evaporated under reduced pressure at 60° C. After dried to be completely cured, it was taken out, pulverized, and through a 40-mesh sieve. Then drying was performed in a vacuum drying oven at 70° C. for 4 hours to obtain solid dispersion granules, and the solid dispersion granules were filled into hard capsules for packaging.

Advantages of the Present Invention

The present invention relates to a process for large-scale preparation of buagafuran API. The purpose of the present invention is to obtain high-purity buagafuran API samples, to clarify the structures of the impurities, and to control the content of the impurities, so that the API samples can be applied in new drug development processes such as clinical research, pharmaceutical research and quality control research.

The present invention is an improvement on the basis of the existing small-scale process to obtain a pilot-scale process for preparing buagafuran samples of over kilogram grade. Specifically, (1) in the present invention, a method for improving the solvent conditions of the dehydration reaction in the existing small-scale process was developed, and the simplification and modification of the subsequent process steps were achieved, including using the one-pot method to perform the three steps of alkylation, reduction and cyclization, and performing the optimization of the reaction conditions and post-treatment operation mode to avoid column chromatography operations and realize the amplification of the pilot-scale process. During the process research, the inventors have unexpectedly discovered that when the compound 5 was prepared by dehydration reaction, if a single system of aqueous phase was used instead of the currently reported water/n-hexane or water/petroleum ether two-phase system for the dehydration reaction, during the subsequent butylation, reduction and cyclization reaction using the one-pot method, the content of the dibutyl-substituted by-product 8 in the system is detected to be only 4.6%, which was significantly lowered compared with the 15% impurity content of the optimal method disclosed in the prior art. Moreover, the inventors have found that the by-product impurity A, which was obtained by the dibutyl by-product 8 subjected to the reaction steps of the subsequent one-pot, only has a content of 1.9% in the crude buagafuran API. (2) In the present invention, it has been found that when hydrochloric acid was added for the final cyclization reaction step to form a bridged ring, impurity B was generated due to the acidity of hydrochloric acid, which was an oxide of buagafuran, and a yield of the impurity B is 1.3%. The impurity A and impurity B are related substances in the preparation process of buagafuran using the method of the present invention, which can be used as comparison substances for impurity detection in the quality control study of buagafuran.

In addition, in the present invention, the refining method of buagafuran is systematically studied, and it is found that the optimal refinement solvent is ethanol, and the cooling temperature of the solution is −20° C. to −10° C. (Table 1). The yield and purity of the buagafuran obtained at this temperature are satisfactory, and the total content of the impurity A and the impurity B after refining can be controlled to less than 0.04%. The method is an efficient and economic refining method.

TABLE 1

Screening results of refining conditions of buagafuran

| Number | Solvent | Dissolving Temperature | Cooling Temperature | Yield | Purity |
|---|---|---|---|---|---|
| 1 | petroleum ether | room temperature | 0° C. | 59.3% | 91.5% |
| 2 | petroleum ether | room temperature | −20° C. to −10° C. | 68.8% | 95.5% |
| 3 | petroleum ether | room temperature | −78° C. (liquid nitrogen) | 75.1% | 91.1% |
| 4 | ethyl alcohol | 40° C. | 0° C. | 56.3% | 92.4% |
| 5 | ethyl alcohol | room temperature | −20° C. to −10° C. | 87.2% | 97.7% |
| 6 | ethyl alcohol | room temperature | −78° C. (liquid nitrogen) | 86.6% | 92.9% |
| 7 | acetone | 40° C. | 0° C. | 47.5% | 94.4% |
| 8 | acetone | room temperature | −20° C. to −10° C. | 43.4% | 93.7% |
| 9 | acetone | room temperature | −78° C. (liquid nitrogen) | 44.1% | 89.6% |

Based on the above-mentioned improvement of the preparation process conditions and the operation mode, the total yield of the obtained buagafuran API was 24.3±5.8%, which was significantly improved compared with the original reported yield of 10.2%. The buagafuran API obtained by the method of the present invention has a purity of greater than or equal to 97.5%, which meets the API quality requirements of the new drug research and development, and can also be used as a standard substance for pharmaceutical research of buagafuran.

What is claimed is:
1. A method of preparing a buagafuran active pharmaceutical ingredient (API) comprising the following steps:
   Step i: reducing a compound 1 to form a compound 2;
   Step ii: oxidizing the compound 2 to form a compound 3;
   Step iii: reacting methyl vinyl ketone with the compound 3 in a cyclization reaction to form a compound 4;
   wherein structures of the compound 1, the compound 2, the compound 3, and the compound 4 are:

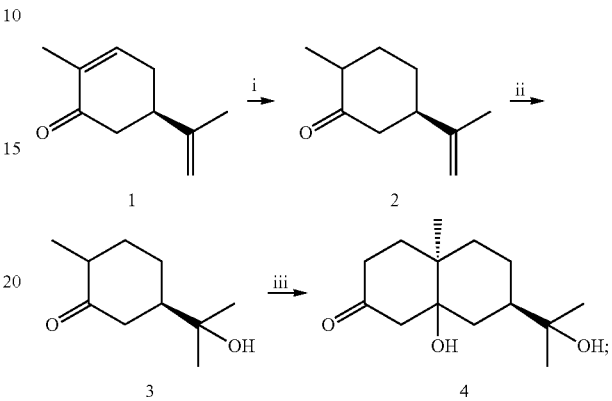

and further comprising:
   Step a: adding the compound 4 to a potassium hydroxide aqueous solution, heating and stirring, then cooling after a reaction is completed to obtain a first mixture, and adding a concentrated hydrochloric acid to adjust a pH of the first mixture to near-neutral and then performing extraction drying, filtration and filtrate concentration to form a compound 5; and
   Step b: dissolving the compound 5 in tert-butanol to obtain a second mixture, adding the second mixture to a potassium hydroxide aqueous solution, heating and stirring, adding bromobutane to obtain a third mixture, adjusting a pH of the third mixture to near-neutral, filtering the third mixture to obtain a first filtrate, concentrating the first filtrate to obtain a concentrate, dissolving the concentrate in methanol, adding sodium borohydride, stirring to obtain a fourth mixture, adding: n-hexane and water to adjust a pH of the fourth mixture to acidity, separating out a n-hexane layer, and concentrating to obtain a crude buagafuran;
   wherein, structures of the compound 4, the compound 5 and the buagafuran are:

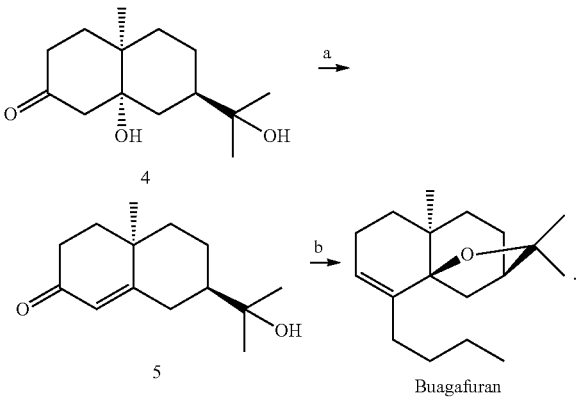

2. The method according to claim 1, further comprising, after the step b, dissolving the crude buagafuran in ethanol, filtering to obtain a filtrate, cooling the filtrate to 10° C. to −20° C., performing a suction filtration to obtain a wet product of refined buagafuran, and drying the wet product to obtain a refined buagafuran API.

\* \* \* \* \*